(12) United States Patent
Mayer-Cumblidge et al.

(10) Patent No.: US 7,776,999 B2
(45) Date of Patent: Aug. 17, 2010

(54) CYANINE-BASED PROBE\TAG-PEPTIDE PAIR FOR FLUORESCENCE PROTEIN IMAGING AND FLUORESCENCE PROTEIN IMAGING METHODS

(75) Inventors: M. Uljana Mayer-Cumblidge, Richland, WA (US); Haishi Cao, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 686 days.

(21) Appl. No.: 11/787,078

(22) Filed: Apr. 12, 2007

(65) Prior Publication Data

US 2008/0254546 A1  Oct. 16, 2008

(51) Int. Cl.
*A61K 38/00* (2006.01)
*C07D 209/04* (2006.01)

(52) U.S. Cl. .................................. 530/300; 548/466
(58) Field of Classification Search ................ 530/300; 548/466

See application file for complete search history.

(56) References Cited

U.S. PATENT DOCUMENTS

| | | | |
|---|---|---|---|
| 6,686,458 B2 | 2/2004 | Tsien et al. | |
| 7,141,655 B2 | 11/2006 | Ebright et al. | |
| 2004/0019104 A1 | 1/2004 | Ebright et al. | |
| 2005/0131217 A1 | 6/2005 | Tsien et al. | |
| 2005/0176065 A1 | 8/2005 | Hanson | |
| 2005/0239135 A1 | 10/2005 | Bogoev et al. | |
| 2006/0141530 A1 | 6/2006 | Ebright et al. | |
| 2006/0141531 A1 | 6/2006 | Ebright et al. | |
| 2006/0147948 A1 | 7/2006 | Keillor et al. | |
| 2006/0147958 A1 | 7/2006 | Koshinsky et al. | |

FOREIGN PATENT DOCUMENTS

| | | |
|---|---|---|
| WO | 03039564 A | 5/2003 |
| WO | 03107010 A | 12/2003 |
| WO | 2006099050 A | 9/2006 |

OTHER PUBLICATIONS

Johnsson, N et al., "A Fusion of Disciplines: Chemical Approaches to Exploit Fusion Proteins for Functional Genomics", ChemBioChem, 2003, vol. 4, pp. 803-810.
Griffin, B. Albert et al., "Specific Covalent Labeling of Recombinant Protein Molecules Inside Live Cells", Science, Jul. 10, 1998, vol. 281, pp. 269-272.
Adams, Stephen R. et al., "New Biarsenical Ligands and Tetracysteine Motifs for Protein Labeling in Vitro and in Vivo: Synthesis and Biological Applications", J. Am. Chem. Soc., 2002, vol. 124, pp. 6063-6076.

*Primary Examiner*—Kamal A Saeed
*Assistant Examiner*—Samantha L Shterengarts
(74) *Attorney, Agent, or Firm*—Wells St. John P.S.

(57) ABSTRACT

A molecular probe comprises two arsenic atoms and at least one cyanine based moiety. A method of producing a molecular probe includes providing a molecule having a first formula, treating the molecule with HgOAc, and subsequently transmetallizing with $AsCl_3$. The As is liganded to ethanedithiol to produce a probe having a second formula. A method of labeling a peptide includes providing a peptide comprising a tag sequence and contacting the peptide with a biarsenical molecular probe. A complex is formed comprising the tag sequence and the molecular probe. A method of studying a peptide includes providing a mixture containing a peptide comprising a peptide tag sequence, adding a biarsenical probe to the mixture, and monitoring the fluorescence of the mixture.

16 Claims, 4 Drawing Sheets

CYANINE-BASED PROBE\TAG-PEPTIDE PAIR FOR FLUORESCENCE PROTEIN IMAGING AND FLUORESCENCE PROTEIN IMAGING METHODS

GOVERNMENT RIGHTS STATEMENT

This invention was made with Government support under Contract DE-AC0676RLO1830 awarded by the U.S. Department of Energy. The Government has certain rights in the invention.

TECHNICAL FIELD

The invention pertains to molecules, molecular probes, and target molecules, methods of producing molecular probes, methods of labeling peptides and methods of studying peptides.

BACKGROUND OF THE INVENTION

Conventional biarsenical probes (probes containing two arsenic atoms) such as FlAsH and ReAsH, which bind a tetracysteine tag incorporated into a protein of interest are utilized as affinity probes. These biarsenical probes have distinct advantages over other multiuse affinity probe systems such as the halo-tag, the SNAP tag, and fluorescent proteins in that the engineered peptide tag is small compared to entire protein domains. This allows utilization in many situations in which a larger tag prevents correct transport of the tag protein or biophysical measurements become inaccurate due to artificial distances.

Biarsenical probes have been utilized in imaging, biophysical fluorescent studies, fluorophore-assisted light inactivation, and for isolation of proteins and protein complexes. In addition to the original probes, FlAsH and ReAsH, improved fluorophores having improved properties have recently been synthesized. However, to date, these probes have equivalent distances between the two arsenic atoms (about 6 Å) and therefore have optimal binding to the same tetracysteine arsenic binding motifs (CysCysProGlyCysCys; SEQ ID NO.3). Accordingly, the two color experiments utilizing such equidistance probes are limited to pulse-chase experiments on a single protein. Researches seeking to study proteins by fluorescence resonance energy transfer (FRET) have been limited to homo-FRET or use of fluorescent proteins as one of the FRET partners.

It would be advantageous to develop alternative biarsenical probes and probe binding peptide motifs.

SUMMARY OF THE INVENTION

In one aspect the invention encompasses a molecule comprising two arsenic atoms and at least one cyanine based moiety.

In one aspect the invention encompasses a molecular probe having formula (I)

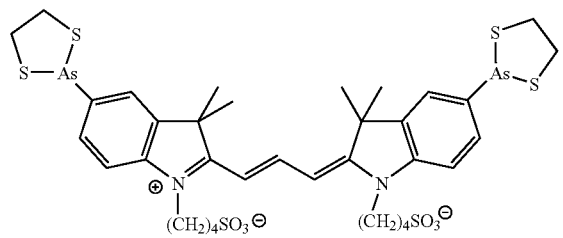

In one aspect the invention encompasses a method of producing a molecular probe. The method includes providing a molecule having formula (II):

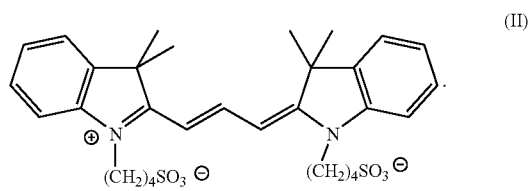

The molecule of formula II is treated with HgOAc and is transmetallized with $AsCl_3$. The As is liganded to ethanedithiol to produce a molecule of formal (I).

In one aspect the invention encompasses a method of labeling a peptide. The method includes providing a peptide comprising SEQ ID NO.2 and contacting the peptide with a molecule of formula (I):

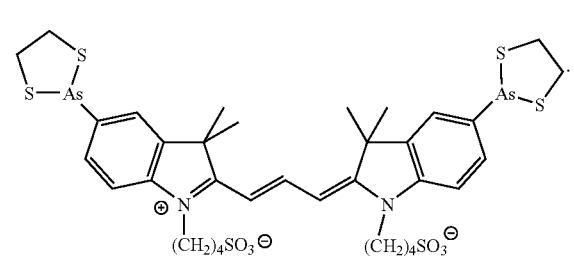

A complex is formed comprising SEQ ID NO.2 and the molecule of formula (I).

In one aspect the invention includes a method of studying a peptide. The method includes providing a mixture containing a peptide comprising SEQ ID NO.2, adding a molecule having formula (I) to the mixture, and monitoring the fluorescence of the mixture.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

Figure 1:
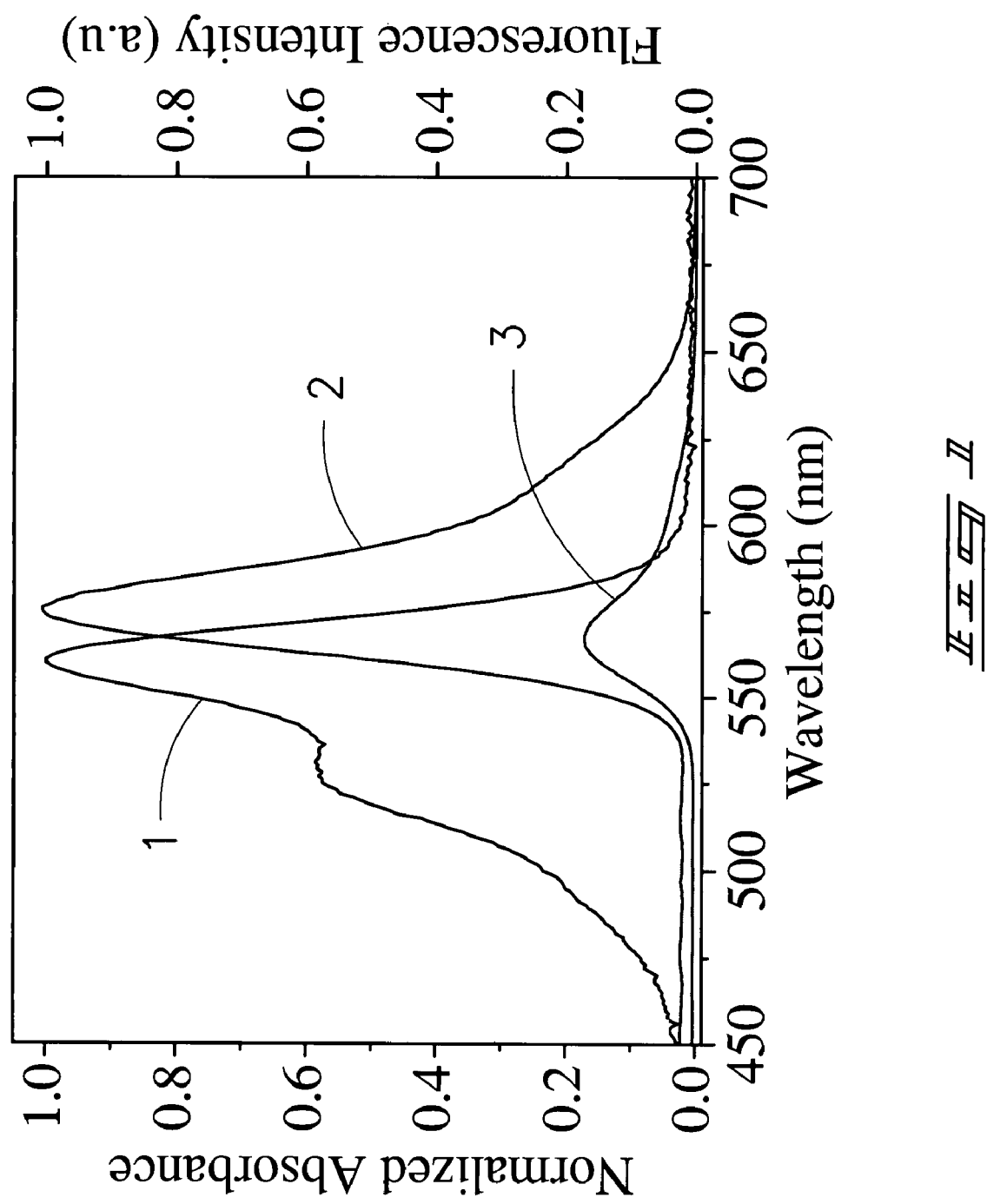
FIG. 1 is a plot of the excitation and emission spectra of a biarsenical probe in accordance with an aspect of the invention in free and bound states.

This disclosure of the invention is submitted in furtherance of the constitutional purposes of the U.S. Patent Laws "to promote the progress of science and useful arts" (Article 1, Section 8).

In general, the invention encompasses affinity probes, methods of making affinity probes and methods of using the affinity probes. The affinity probes of the invention have two arsenic atoms and can therefore be referred to as biarsenical probes. In accordance with the invention an affinity probe refers to a molecule having affinity for one or more tag molecules. The "probe" aspect of the molecule indicates that it can be utilized to report binding of the probe molecule to the tag molecule.

In contrast with conventional existing biarsenical probes which typically are based upon a fluorescein or alternative xanthene-based fluorophore moiety and have a distance between the two arsenic atoms of about 6 Å, biarsenical probes in accordance with the invention indocyanine dye-based and have a longer distance between the two arsenic atoms. Accordingly, rather than binding the typical conventional "tetracysteine arsenic grasp" (TAG) motifs (Cys CysProGlysCysCys; SEQ ID NO. 3) the biarsenical probes of the invention can be utilized with alternative amino acid tag sequences (discussed further below).

Rather than the six amino acid tetra-cysteine tag motif utilized in conjunction with conventional biarsenical probes, alternative tag sequences can be utilized in conjunction with the biarsenical probes of the invention. In one aspect, the tag can have two cysteine pairs separated by a distance of about 14 Å upon alpha helical formation of intervening amino acid sequence between the cysteine pairs. In other words, upon alpha helical formation of the tag, the two cysteine pairs can preferably be two helical turns apart on the alpha helix resulting in a 14 Å distance (approximately) based upon the published NMR structure for an alanine-lysine alpha helix. Accordingly, the inter-cysteine pair distance is approximately equivalent to the inter-arsenic distance of the biarsenical probe.

Peptide tags of the invention can be covalently linked by, for example, peptide bonding to a protein or peptide of interest. Such can be achieved by, for example, chemical or conventional molecular biology techniques. The tag can be linked to an n-terminal or c-terminal of a peptide of interest or can alternatively be integrated within the amino acid sequence of the protein of interest. The covalently linked tag can allow studying of the peptide or protein of interest and can be utilized for studying properties such as conformation, protein interaction, protein localization, quantification and protein folding. Such studies can be performed in vitro or in vivo as appropriate.

In general, formation of the biarsenical probes in accordance with the invention can be performed by providing a molecule of formula (III) (for chemical structures of formulas I, II, and III, see below) and reacting the compound of formula (III) with triethylorthoformate. The providing of the molecule of formula (III) can comprise, for example, synthesizing the molecule of formula (III) by reacting a mixture of 2,3,3-trimethyl-indole and 1,4-butane sultone. Reacting the compound of formula (III) with triethylorthoformate can be utilized to produce the compound having formula (II). The compound of formula (II) can be treated by, for example, metallization with mercury. Such metallization can be achieved, for example, by treating the molecule of formula (II) with mercuric oxide. The resulting metallized molecule can then be transmetallized to replace the mercury with arsenic. Transmetallization can be achieved, for example, by treating the metallized molecule with arsenic trichloride. The transmetallized molecule can subsequently be liganded to ethanedithiol to produce the molecule having formula (I). The liganding can be performed by, for example, treating the transmetallized molecule with 1,2-ethanedithiol. An exemplary synthesis is described in detail below.

Synthesis of the biarsenical probes of the invention can be performed as follows.

During synthesis, all synthetic manipulations were performed under dry argon atmosphere using standard techniques. A mixture of 2,3,3-trimethyl-indole (0.80 g, 5 mmol) and 1,4-butane sultone (2.25 g, 16 mmol) and 7 mL of 1,2-dichlorobenzene was refluxed at 120° C. for 12 hr under an argon atmosphere. After cooling, the reaction mixture was dropped into cold acetone (100 mL) and the precipitate was collected. 1-δ-sulfobutyl-2,3,3-trimethyl-indolenine (pink powder) was washed with acetone (20 mL) 3 times. The yield was 69%.

The resulting compound was confirmed by NMR to be formula (III):

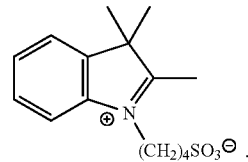

$^1$H NMR (DMSO): 1.19 (s, 6H), 1.39 (t, J=7.3, 2H), 1.61 (m, 2H), 2.10 (m, 2H), 3.07 (s, 3H), 4.13 (t, J=4.5, 2H), 7.27 (m, 2H), 7.49 (t, J=4.0, 1H), 7.69 (d, J=6.5, 1H). $^{13}$C NMR (DMSO): 14.53, 22.68, 22.84, 26.78, 48.01, 50.81, 54.82, 116.23, 124.16, 129.71, 130.17, 141.89, 142.64. ESI/MS: m/z calcd. for [M+H]+708.84, found 709.12.

Compound formula (III) (100 mg, 0.34 mmol, 1 equivalent) and triethylorthoformate (101 mg, 0.68 mmol, 2 equivalent) were heated together in a buffered acetic anhydride/acetic acid mixture (1.5 mL acetic acid, 1.13 mL acetic anhydride and 0.065 g sodium acetate) at 120° C. for 12 hours at which time the solvent was removed and the residue was dissolved in methanol. 3-(3,3-dimethyl-1-(4-sulfobutyl)indolin-2-ylidene)prop-1-enyl)-3,3-dimethyl-1-)-4-sulfobutyl)3H-indolium, compound formula (II):

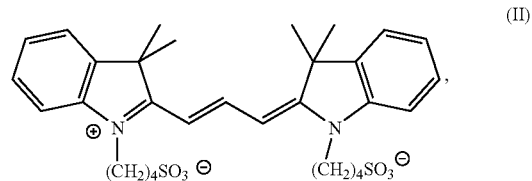

(II)

was purified by silica gel thin layer chromatography (TLC) utilizing ethyl acetate: methanol at a 6:5 volume:volume ratio with 90% yield, and was characterized using NMR. $^1$H NMR (DMSO): 3.55 (m, 8H), 6.15 (d, J=7.2, 2H), 6.81 (d,J=6.8, 2H), 7.08 (d, J=6.0, 1H), 8.03 (d, J=6.4, 2H), 8.60 (m, 1H). $^{13}$C NMR (DMSO):22.4, 27.3, 28.2, 44.3, 48.9, 49.1, 51.8, 103.3, 112.2, 123.1, 125.9, 129.7, 141.5, 142.8, 150.7, 174.6. ESI/MS: m/z calcd. for [M+H]+708.84, found 709.12.

The molecule having formula (II) is hereinafter interchangeably referred to as Cy3.

189 mg of Cy3 (0.30 mmol, 1 equivalent) was added into trifluoroacetic acid (4 mL) containing mercuric oxide (216 mg, 0.60 mmol, 2 equivalent) at room temperature. After overnight stirring, the reaction mixture was evaporated. A pink precipitate (Cy3-bis-mercuric trifluoroacetate, 304 mg) was collected by filtration with a 75% yield. After drying in high vacuum the bis-mercuric trifluoroacetate derivative (304 mg) was resuspended in dry N-methyl pyrrolidinone (3.5 mL) with arsenic trifluoride (300 μL, 6.2 mmol, 27 equivalents), di-isopropyl ethyl amine (220 μL, 2.3 mmol, 10 equivalents) and catalytic palladium acetate (20 mg) to perform the transmetallization from mercury to arsenic. The reaction was stirred at room temperature for 8 hours. After 8 hours, 10 mL of 0.25 M phosphate buffer pH 7 and 1,2-ethanedithiol (10 mmol, 44 equivalents) was added to the reaction mixture. The solution was subsequently extracted with $CHCl_3$ (3×30 mL) and was dried over $Na_2SO_4$, evaporated and purified by silica gel chromatography utilizing a methanol:toluene solvent system at a 1:2 volume:volume solvent ratio with an 81% yield of compound formula (I):

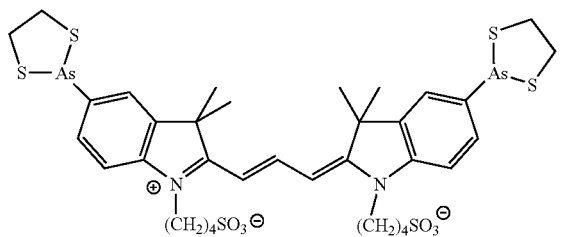

as characterized by NMR. $^1$H NMR (DMSO): 3.55 (m, 8H), 6.15 (d, J=7.2, 2H), 6.81 (d,J=6.8, 2H), 7.08 (d, J=6.0, 1H), 8.03 (d, J=6.4, 2H), 8.60 (m, 1H). $^{13}$C NMR (DMSO):22.4, 27.3, 28.2, 44.3, 48.9, 49.1, 51.8, 103.3, 112.2, 123.1, 125.9, 129.7, 141.5, 142.8, 150.7, 174.6. ESI/MS: m/z calcd. for [M+H]+708.84, found 709.12

The overall yield of the resulting molecule having formula 1 was 37.9%.

Alternative synthetic routes were also utilized and compared with the above described synthetic route. For example, attachment of the arsenic to the cyanine subunits prior to creating the linker region or synthesis of the linker region with base proved far lower yielding relative to the above described reaction route. It is to be understood however that the invention contemplates utilization of alternative synthetic routes.

In addition to NMR, the synthesized probe of formula (I) was characterized by determining the absorbance (line 1) and emission (line 3) spectra, as presented in FIG. 1. The free probe has an absorbance maximum at 560 nm and an emission maximum at 568 nm. The absorbance spectrum does not change upon ethanedithiol release and tag binding (discussed below).

In one aspect the invention encompasses affinity tags which bind to probes encompassed by the invention. The affinity tags can comprise two pair of cysteines separated by a minimum of three amino acids. Typically, the two pair of cysteines will be separated by more than three amino acids such as, for example, five amino acids. The three or more amino acids separating the two cysteine pairs are not limited to any particular amino acids or sequence of amino acids.

Where five amino acids separate the cysteine pairs, the overall tag sequence can be SEQ ID NO.:4, where Xaa=any amino acid. In particular embodiments it can be preferable that the overall tag sequence has the propensity to form an alpha-helix and amino acids denoted by Xaa in SEQ ID NO.:4 can be chosen accordingly, as will be understood by those skilled in the art. In particular applications the cysteine pairs can be separated by an amino acid sequence LysAlaGlu AlaAla (SEQ ID NO.1) to produce an affinity tag having an overall sequence CysCysLysAlaGluAlaAlaCysCys (SEQ ID NO.2).

Affinity studies utilizing the affinity between the probes and tags of the invention can be useful for studying a variety of protein characteristics and interactions as discussed above. The peptide tag can be synthesized independently of a protein of interest, or can be synthesized by adding amino acids chemically onto the sequence of a protein of interest. Alternatively, a pre-synthesized tag can be chemically joined to a C-terminus of a protein of interest, to an N-terminus of a protein of interest, or integrated within the amino acid sequence of a protein of interest. Additionally, as will be understood by those of ordinary skill in the art, conventional genetic manipulation techniques can be utilized to biologically produce a recombinant protein of interest having the tag integrated within the sequence of the protein of interest or adjoining the protein of interest at the C-terminal or N-terminal region. Further, the invention is not limited to single tags and contemplates utilizing two or more tags in association with a protein of interest.

Figure 4A:
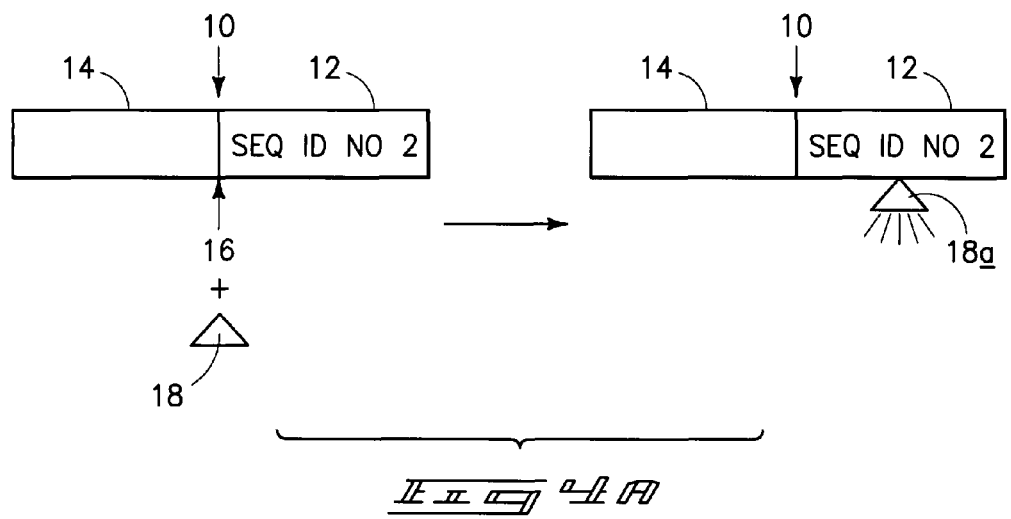
FIG. 4A is a diagrammatic illustration of a probe binding study in accordance with one aspect of the invention.

Referring to FIG. 4A, methodology of the present invention can involve labeling a peptide by providing a peptide 10 comprising a tag sequence 12, including but not limited to SEQ ID NO.2, linked to a peptide or protein of interest 14. Although FIG. 4A shows tag 12 being linked at the C-terminal end 16 of peptide of interest 14, it is to be understood that the invention also contemplates the tag sequence being linked to the N-terminal of peptide 14.

A composition can be formed by adding a probe 18, which can be, for example, biarsenical formula (I) as described above. Probe 18 can bind specifically to tag 12 to form a complex with increased fluorescence (denoted by subscript 'a' on numeric identifier 18), such that complex formation can be monitored by monitoring the fluorescence.

Figure 4B:
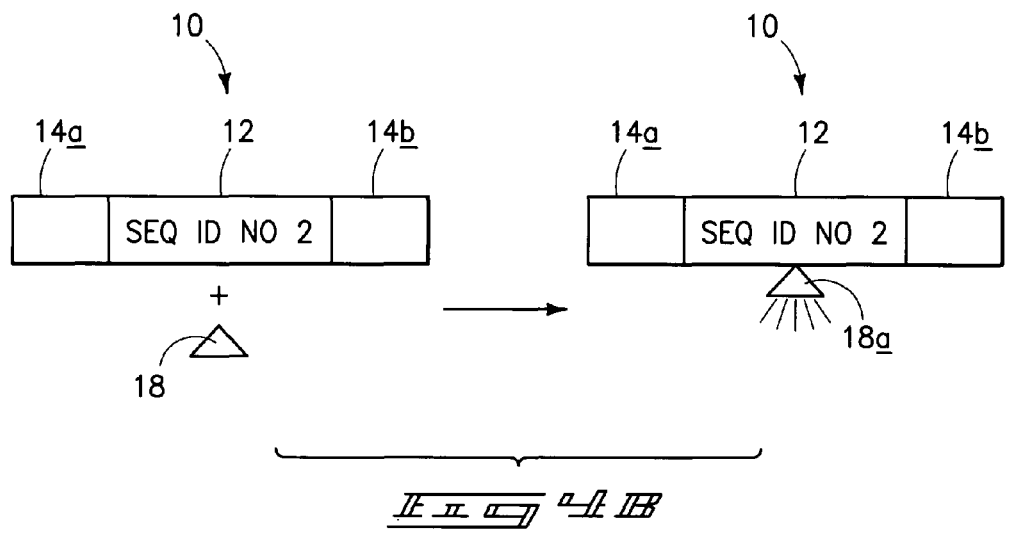
FIG. 4B is a diagrammatic illustration of a probe binding study in accordance with another aspect of the invention.

As shown in FIG. 4B, tag sequence 12 can be integrated within the amino acid sequence of a protein of interest such that a first portion 14a of the peptide of interest is followed by tag 12 which is followed by a second portion 14b of the peptide of interest (where portions 14a and 14b are not limited to any particular length and can be individually up to the full length of the protein of interest). Probe 18 can specifically bind to the tag in the integrated form of the tag resulting in an increase in fluorescence. Fluorescence studies in accordance with the invention can be performed in vitro, extracellularly and in specific applications can be performed within a cell.

Figure 2:
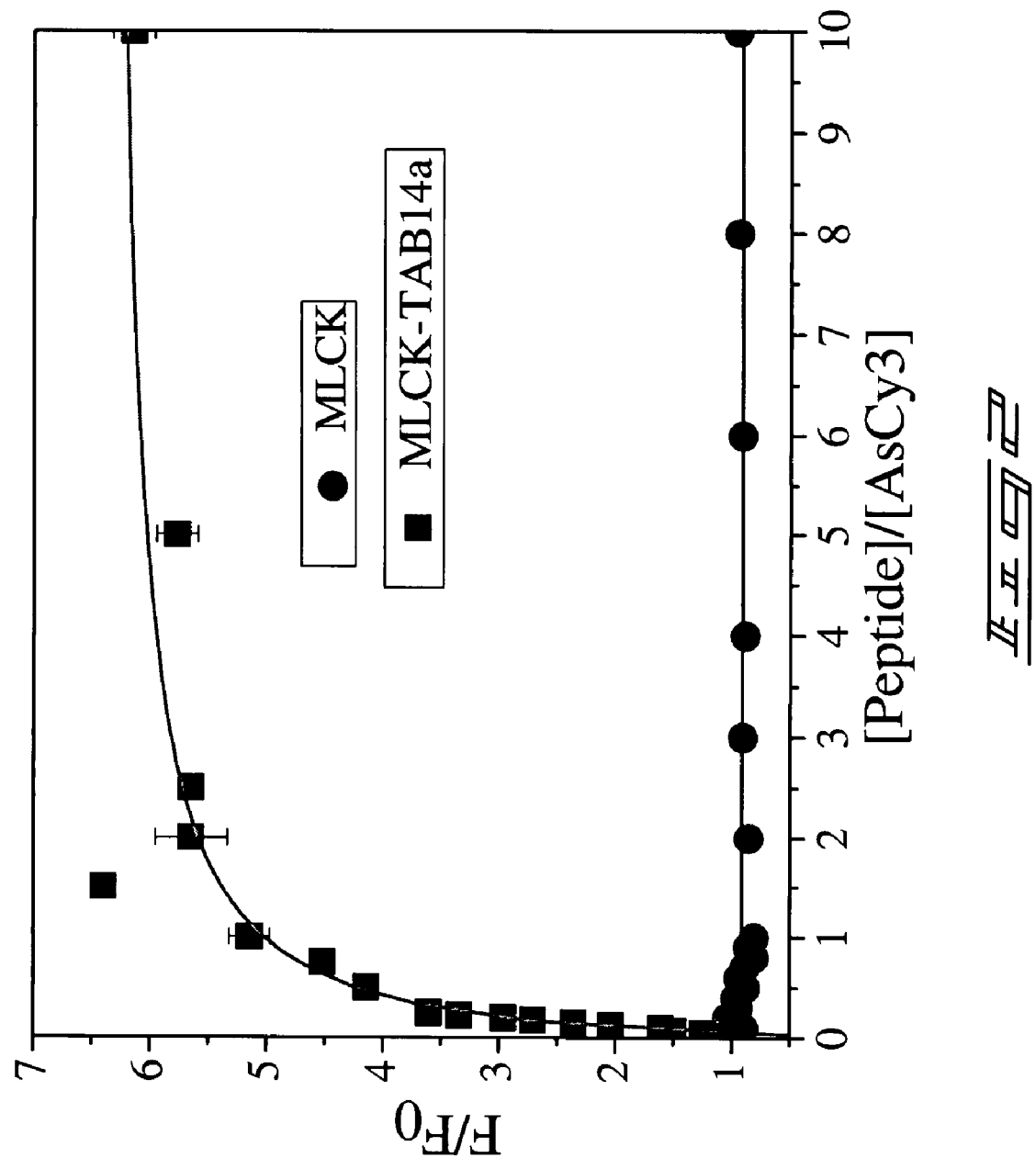
FIG. 2 shows titration of a biarsenical probe in accordance with one aspect of the invention with the calmodulin binding peptide of myosin light chain kinase with (squares) and without (circles) the probe-binding tag sequence.

For the present study, a tagged peptide was created utilizing the calmodulin binding peptide of the myosin light chain kinase (MLCK) having SEQ ID NO.2 engineered onto the C-terminus (henceforth tagged MLCK peptide). To determine the binding affinity of the probe to the tag, the tagged MLCK peptide was titrated into a solution containing a probe having formula (I). As shown in FIG. 2, upon addition of the tagged peptide (squares) the fluorescence of the probe increased 5.8 fold. When the titration curve was fitted through the Hill equation an apparent $K_d$ of 0.91 mmol and an N of 0.99 were determined in the presence of 100 mmol ethanedithiol. These values are comparable to the apparent $K_d$ of FlAsH-FlAsHTAG binding of 3 mmol in the presence of 200 mmol ethanedithiol. This corresponds to peak molar binding in the absence of ethanedithiol. The curve fit shows that the probe and peptide bind in a 1:1 ratio. Non-tagged MLCK peptide (circles) was utilized as control to titrate the probe and yields no increase in fluorescence.

Referring again to FIG. 1, such figure additionally shows the absorbance spectra of the bound probe/tagged MLCK peptide pair also indicated by line 2; and the fluorescence spectra of the probe/tagged MLCK peptide pair indicated by the solid line. The spectra of FIG. 1 are normalized to the probe/tagged MLCK peptide pair.

As indicated by FIG. 1, while the absorbance spectra does not change upon ethanedithiol release and peptide tag binding, the fluorescence spectra red-shifts to a maximum of 576 nm. The tag bound probe has a quantum yield of 0.28. With the very high extinction coefficient of 180,000 the yield of brightness is similar to that of FlAsH (reported 41-60 depending on binding peptide) and considerably higher than ReAsH. The lifetime of peptide bound probe is three times longer than that of FlAsH under photo bleaching conditions.

Figure 3:
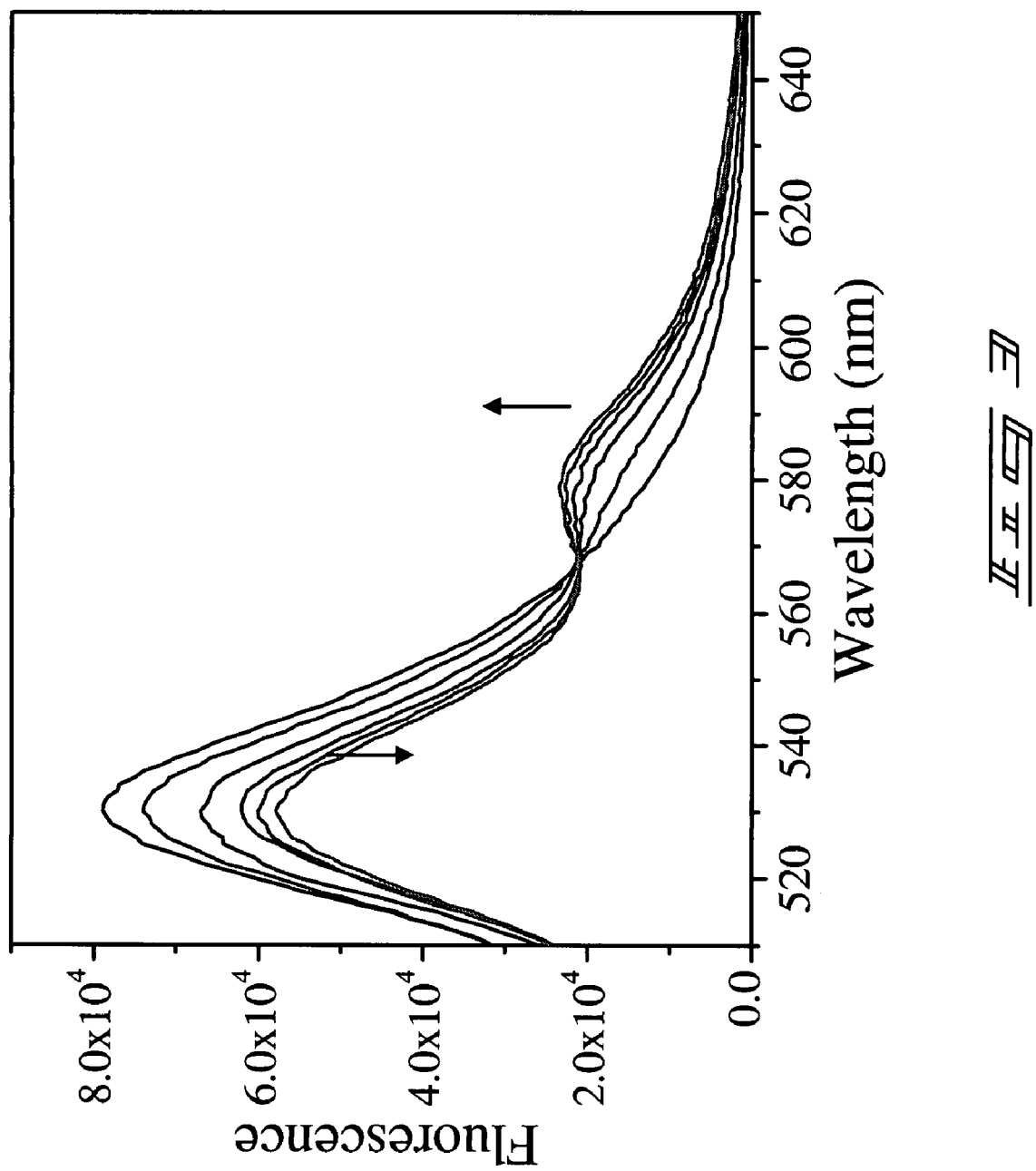
FIG. 3 shows titration of FlAsH-labeled calmodulin with 0.1-1 μM biarsenical probe labeled peptide.

Fluorescent resonance energy transfer (FRET) studies were also performed. Calmodulin which is known to bind MLCK in a 1:1 ratio in the presence of calcium was covalently linked to a FlAsH-tag having sequence CysCysProGlyCysCys (SEQ ID NO.3). SEQ ID NO.2 was utilized to label the MLCK peptide as described above. The tagged MLCK peptide and the FlAsH-tag calmodulin were reacted with FlAsH and the probe of the invention (formula (I)) in a single pot to demonstrate selective labeling. The results of labeling experiments are shown in FIG. 3.

The FRET results show a better than 85/15 preference for formula (I) binding of the peptide-tag over FlAsH tag binding which is subsequently bound by the FlAsH probe. When the FlAsH labeled calmodulin was titrated with tagged MLCK peptide labeled with the formula (I) probe, FRET was observed in proportion to labeling (FIG. 3) indicating that the FlAsH probe and formula (I) probe function as a FRET pair.

The results above indicate that the new biarsenical fluorescent probes of the invention have strong photostability, low pH sensitivity and a high absorbance and quantum yield. The probe is directed to and has specificity to small tetracysteine binding tags including specificity to those tags relative to existing smaller tetracysteine tags. The probes of the invention additionally provide excellent FRET partners to the biarsenical dye FlAsH, making the probes an important step towards a whole toolkit of colored probes directed toward differing small binding motifs.

In addition to the probe described above, the invention includes additional biarsenical probes capable of binding peptide sequences of various lengths and/or sequence. In general, the probes differ from one another in their ring systems, at the linker region (between the ring moieties), in substitution of the linker or ring systems, or in substitution of the nitrogen atoms. The probes generally fit one of two general formulas A and B below.

Formula A:

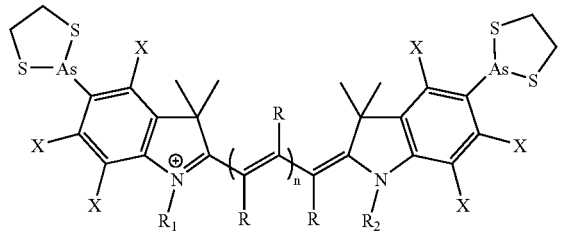

Formula B:

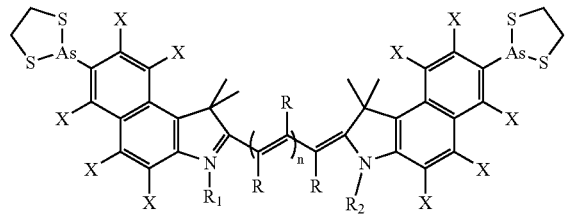

where R1 and R2 are independently selected from alkyls, alkyl chains with a solubilizing group (e.g. sulfonated), an alkyl linker attached to a support, an alkyl linker attached to a crosslinking moiety, and part of a stabilizing ring system; R is H or part of a stabilizing ring system; and X is each independently H, F, Cl, Br, nitrate, or sulfonate.

Specific examples of probes in accordance with these general formulas are set froth below. However, these examples are in no way intended to limit the scope of the invention or the present application.

EXAMPLE 1

2-((1E,3E)-3-(7-(1,3,2-dithiarsolan-2-yl)-1,1,3-trimethyl-1H-benzo [e]indol-2(3H)-ylidene)prop-1-enyl)-7-(1,3,2-dithiarsolan-2-yl)-1,1,3-trimethyl-1H-benzo[e]indolium

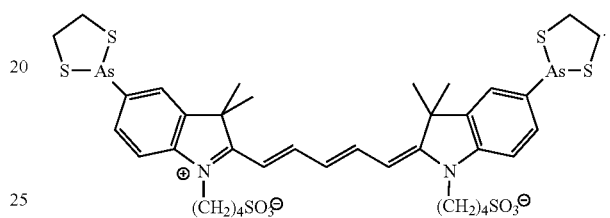

A: A mixture of 2,3,3-trimethyl-indole (0.80 g, 5 mmol) and 1,4-butane sultone (2.25 g, 16 mmol) in 7 mL of 1,2-dichlorobenzene was refluxed at 120° C. for 12 hr under an Argon atmosphere. After cooling, the reaction mixture was dropped into cold acetone (100 mL) and the precipitate was collected. 1-δ-Sulfobutyl-2,3,3-trimethyl-indolenine (pink powder) was washed with acetone (20 mL) three times. The yield was 69%.

B: The compound from Step A (296 mg, 1 mmol, 1 eq.) and N,N'-(propane-1,3-diylidene)dianiline hydrochloride (259 mg, 1 mmol, 1 eq.) were heated together in a buffered acetic anhydride/acetic acid mixture (1.5 mL acetic acid, 1.13 mL acetic anhydride and 0.065 g sodium acetate) at 120° C. for 12 hrs. After the reaction, the solvent was removed and the residue was dissolved in MeOH. 2-(5-(3,3-dimethyl-1-(4-sulfobutyl)indolin-2-ylidene)penta-1,3-dienyl)-3,3-dimethyl-1-(4-sulfobutyl)-3H-indolium (2) was purified by silica gel thin layer chromatography (TLC; ethyl acetate: MeOH=2:1 v/v) with 90% yield.

C: The compound from Step B (265 mg, 0.40 mmol, 1 eq.) was added into trifluoroacetic acid (4 mL) containing mercuric oxide (173 mg, 0.80 mmol, 2 eq.) at room temperature. After overnight stirring, the reaction mixture was evaporated. Blue precipitate (compound from step B-bis-mercuric trifluoroacetate, 320 mg) (3) was collected by filtration with 75% yield. After drying in high vacuum, compound from step B-bis-mercuric trifluoroacetate (320 mg) was suspended in dry N-methylpyrrolidinone (3.0 mL) with arsenic trichloride (400 uL, 8.3 mmol, 30 eq.), diisopropyl ethyl amine (315 uL, 3.4 mmol, 10 eq.) and catalytic palladium acetate (30 mg). The reaction was stirred at room temperature for 8 hours. After reaction, 10 mL 0.25M phosphate buffer pH 7 and 1,2-ethanedithiol (10 mmol, 44 eq.) were added into reaction mixture. The solution was extracted with CHCl$_3$ (3×30 mL), dried over Na$_2$SO$_4$, evaporated and purified by chromatography on silica gel (MeOH: toluene=1:2 v/v) with an 81% yield.

EXAMPLE 2

2-((1E,3E)-3-(7-(1,3,2-dithiarsolan-2-yl)-1,1,3-trimethyl-1H-benzo[e]indol-2(3H)-ylidene)prop-1-enyl)-7-(1,3,2-dithiarsolan-2-yl)-1,1,3-trimethyl-1H-benzo[e]indolium

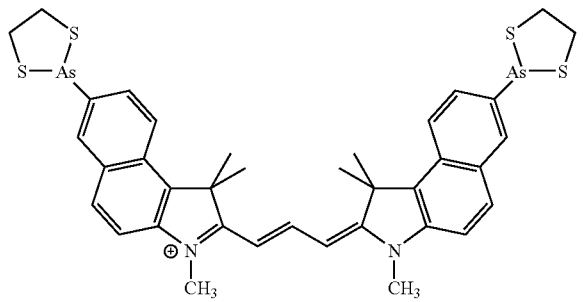

A: A mixture of 2,3,3-trimethyl-indole (5 g, 24 mmol) and methyl iodide (6.79 g, 48 mmol) in 50 mL of acetonitrile was refluxed at 120° C. for 30 min under a Argon atmosphere. After cooling, the product precipitated and was collected from solution. 1,1,2,3-tetramethyl-1H-benzo[e]indolium (white powder) was recrystallized using ethanol (20 mL) three times, yield 80%.

B: The compound from Step A (2 g, 9 mmol, 1 eq.) and triethyl orthoformate (2.64 g, 18 mmol, 2 eq.) were heated to refluxing in pyridine for 9 hrs. After the reaction, the solvent was removed and the residue was dissolved in MeOH. Product was purified by silica gel TLC (ethyl acetate: MeOH=2:1 v/v) with 73% yield.

C: The compound from Step B (43 mg, 0.08 mmol, 1 eq.) was added into trifluoroacetic acid (3 mL) containing mercuric oxide (90 mg, 0.4 mmol, 5 eq.) at room temperature. After overnight stirring, the reaction mixture was evaporated. Blue precipitate was collected by filtration with 82% yield. After drying in high vacuum, 100 mg was suspended in dry N-methylpyrrolidinone (1.5 mL) with arsenic trichloride (100 uL, 2.0 mmol, 30 eq.), diisopropyl ethyl amine (83 uL, 0.8 mmol, 10 eq.) and catalytic palladium acetate (30 mg). The reaction was stirred at room temperature for 8 hours. After reaction, 10 mL 0.25M phosphate buffer pH 7 and 1,2-ethanedithiol (0.4 mL, 44 eq.) were added into reaction mixture. The solution was extracted with $CHCl_3$ (3×30 mL), dried over $Na_2SO_4$, evaporated and purified by chromatography on silica gel (MeOH:toluene=2:1 v/v) with a 37% yield.

EXAMPLE 3

2-((1E,3E,5E,7E)-7-(5-(1,3,2-dithiarsolan-2-yl)-1,3,3-trimethylindolin-2-ylidene)hepta-1,3,5-trienyl)-5-(1,3,2-dithiarsolan-2-yl)-1,3,3-trimethyl-3H-indolium

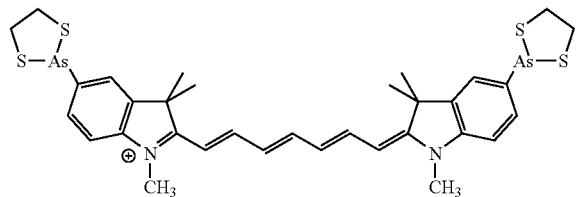

1,3,3-trimethyl-2-((1E,3E,5E,7E)-7-(1,3,3-trimethylindolin-2-ylidene)hepta-1,3,5-trienyl)-3H-indolium (200 mg, 0.4 mmol, 1 eq.) was added into trifluoroacetic acid (5 mL) containing mercuric oxide (201 mg, 1 mmol, 2.5 eq.) at room temperature. After overnight stirring, the reaction mixture was evaporated. Red precipitate (Ay7-bis-mercuric trifluoroacetate, 300 mg) was collected by filtration with 75% yield. After drying in high vacuum, Cy7-bis-mercuric trifluoroacetate (100 mg) was suspended in dry N-methylpyrrolidinone (1.5 mL) with arsenic trichloride (100 uL, 2.0 mmol, 20 eq.), diisopropyl ethyl amine (83 uL, 0.8 mmol, 8 eq.) and catalytic palladium acetate (30 mg). The reaction was stirred at room temperature for 8 hours. After reaction, 10 mL 0.25M phosphate buffer pH 7 and 1,2-ethanedithiol (0.4 mL, 40 eq.) were added into reaction mixture. The solution was extracted with $CHCl_3$ (3×30 mL), dried over $Na_2SO_4$, evaporated and purified by chromatography on silica gel (MeOH:ethyl acetate=1:2 v/v) with a 15% yield.

EXAMPLE 4

1-(3,3-diethoxypropyl)-2-((1E,3Z)-3-(1-(3,3-diethoxypropyl)-3,3-dimethylindolin-2-ylidene)prop-1-enyl)-3,3-dimethyl-3H-indolium

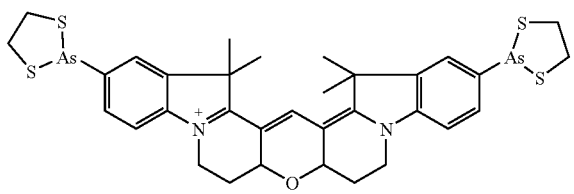

A: To a stirred solution of 2,3,3-trimethyl-indole (1.44 g, 9.3 mmol) in ethanol (40 mL) at ambient temperature was added hydrobromic acid (3.16 mL of 48% aqueous solution). After 1 hour the reaction solvent was removed. The hydrobromide salt was redisolved in acetonitrile (20 mL) and acetic acid (100 mL) and arolein diethyl acetal (18.2 g, 140 mmol) added. The reaction mixture was warmed to 70° C. for 20 minutes. The solution was cooled and the reaction solvent removed. The product was purified by TLC (ethyl acetate: MeOH=4:1 v/v), yield 30%.

B: To stirred solution of the compound from Step A (356 mg, 0.95 mmol) in pyridine (10 mL) at 120° C. was added dropwise, triethyl orthoformate (98 mg, 66 mmol) over 30 min. After 2 hr the reaction mixture was cooled. The product was purified by TLC with 30% yield.

Since the length of the linker region, and/or the ring systems may vary, the distance between the arsenic atoms will also differ between probes of the invention. Additionally these differences and/or differences in substitutions may provide affinity to various differing amino acid sequences. Particular probes, for example, may have high affinity for amino acid sequences having a specific number of amino acids between the cysteine pair, and can additionally have increased affinity for a particular sequence of amino acids between the cysteine pair.

In general, probes of the invention can be used to bind free peptides, or peptide tags which have been incorporated into a protein of interest where the free peptide or tag has all or at least a two cysteine portion of the sequence $Xaa_{n1}CysXaa_{n2}CysXaa_{n3}CysXaa_{n4}CysXaa_{n5}$, where n1 through n5 are independently or dependently 0 through 50.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. A molecule consisting of formula (A)

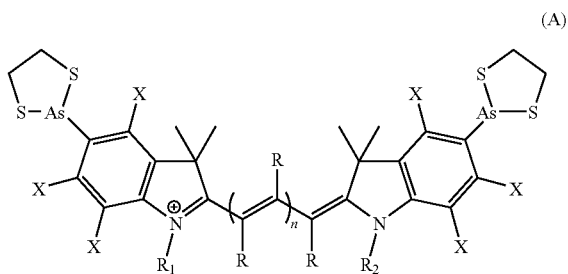

where R1 and R2 are independently selected from alkyls, alkyl chain with a solubilizing group, or part of a stabilizing ring system; R is H or part of a stabilizing ring system; n is 0 or a positive integer; and X is each independently H, F, Cl, Br, nitrate, or sulfonate.

2. The molecule of claim 1 wherein the molecule has the formula (A1)

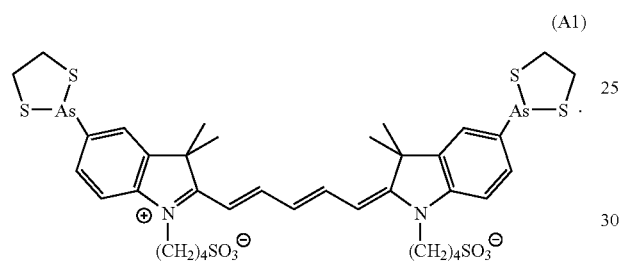

3. The molecule of claim 1 wherein $R_1$ and $R_2$ are methyl.

4. The molecule of claim 3 wherein the molecule has the formula (A2)

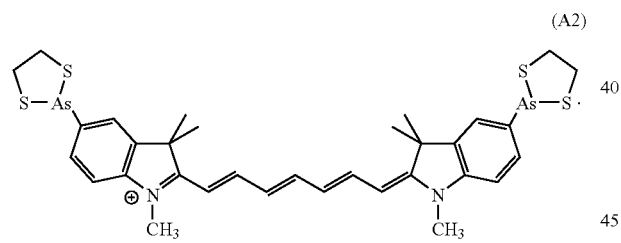

5. The molecule of claim 1 wherein the molecule has the formula (A3)

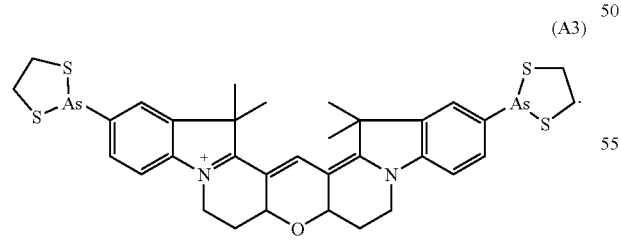

6. The molecule of claim 1 wherein the spatial distance between the two arsenic atoms is about 14.5 Å.

7. The molecule of claim 1 wherein the molecule specifically reacts with a target amino acid sequence to generate a detectable fluorescent signal.

8. The molecule of claim 7 wherein the amino acid sequence comprises two pairs of peptide bonded cysteines.

9. The molecule of claim 8 wherein the two pairs of cysteines are separated from one another by a series of at least three amino acids.

10. The molecule of claim 9 wherein the two pairs of cysteines are separated from one another by a series of amino acids having SEQ ID NO: 1.

11. A molecular probe having structure (B)

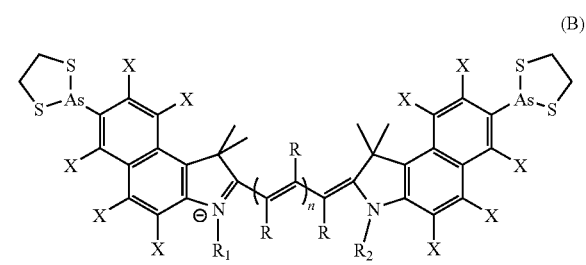

where R1 and R2 are independently selected from alkyls, alkyl chains with a solubilizing group, and a part of a stabilizing ring system; n is 0 or a positive integer; R is H or part of a stabilizing ring system; and X is each independently H, F, Cl, Br, nitrate, or sulfonate.

12. The molecule of claim 10 having a formula (B1)

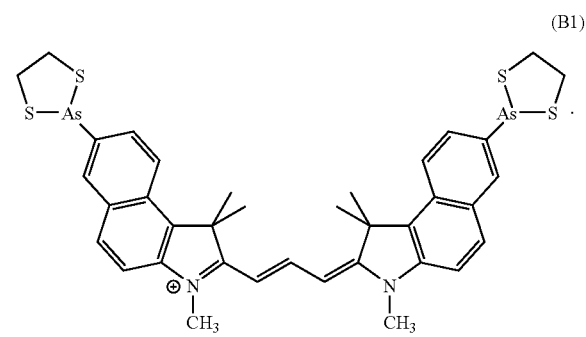

13. A molecular probe having formula (I):

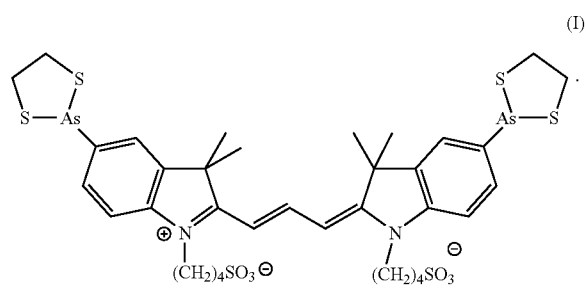

14. A method of producing a molecular probe comprising: providing a molecule having formula (II),

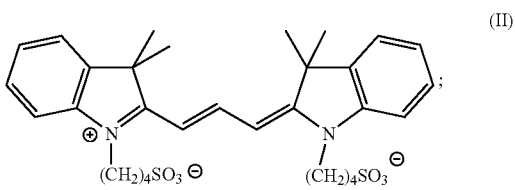

treating the molecule of formula (II) with HgOAc; transmetallizing the Hg treated molecule with AsCl₃; and liganding the As to ethanedithiol to produce a molecule of formula (I), (I)

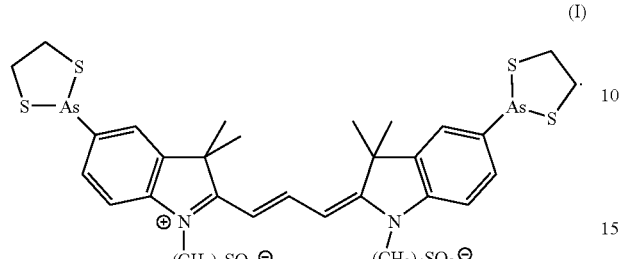

15. A probe/peptide complex comprising:
a probe consisting of formula (A)

(A)

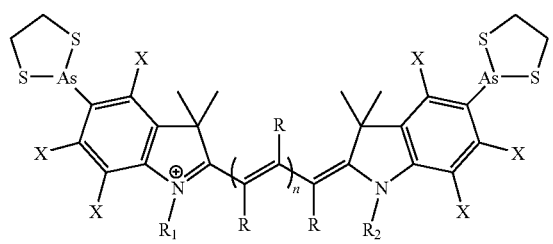

where R1 and R2 are independently selected from alkyls, alkyl chains with a solubilizing group, or part of a stabilizing ring system; n is 0 or a positive integer; R is H or part of a stabilizing ring system; and X is each independently H, F, Cl, Br, nitrate, or sulfonate; and a peptide having sequence CysXaa$_{n1}$Cys, where n1 is from 1 to 50 amino acids.

16. A probe/peptide complex comprising:
a probe consisting of formula (B)

(B)

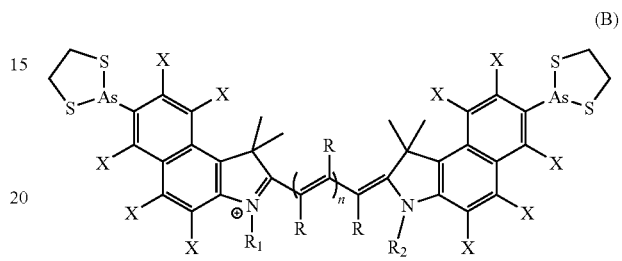

where R1 and R2 are independently selected from alkyls, alkyl chains with a solubilizing group, or part of a stabilizing ring system; n is 0 or a positive integer, R is H or part of a stabilizing ring system; and X is each independently H, F, Cl, Br, nitrate, or sulfonate; and a peptide having sequence CysXaa$_{n1}$Cys, where n1 is from 1 to 50 amino acids.

* * * * *

UNITED STATES PATENT AND TRADEMARK OFFICE
CERTIFICATE OF CORRECTION

| | |
|---|---|
| PATENT NO. | : 7,776,999 B2 |
| APPLICATION NO. | : 11/787078 |
| DATED | : August 17, 2010 |
| INVENTOR(S) | : M. Uljana Mayer-Cumblidge and Haishi Cao |

It is certified that error appears in the above-identified patent and that said Letters Patent is hereby corrected as shown below:

54 Title – Insert --A-- before the word "Cyanine-Based" at the beginning of the title Column 1, line 42 – Replace "researches" with --researchers--

Column 5, line 28 – Replace "(d,J=6.8, 2H)" with --(d, J=6.8, 2H)--

Column 7, Formula B – Replace:

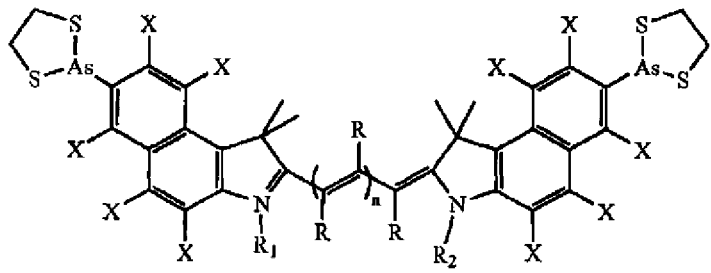

With:

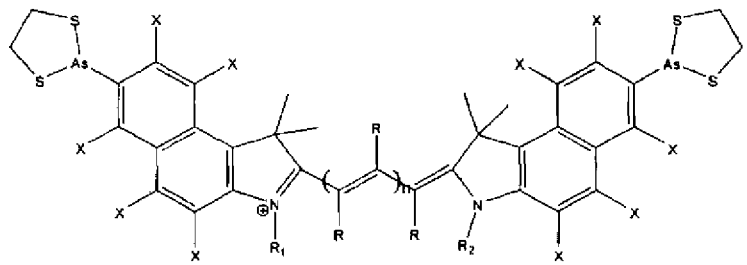

Column 7, line 64 – Capitalize "where" at the beginning of the sentence

Column 8, line 59 – Replace "400 uL" with --400 μL--

Column 8, line 59 – Replace "diisopropyl" with --di-isopropyl--

Signed and Sealed this
Twenty-ninth Day of May, 2012

David J. Kappos
*Director of the United States Patent and Trademark Office*

CERTIFICATE OF CORRECTION (continued)
U.S. Pat. No. 7,776,999 B2

Column 8, line 59 – Replace "315 uL" with --315 μL--

Column 9, line 38 – Replace "100 uL" with --100 μL--

Column 9, line 39 – Replace "diisopropyl" with --di-isopropyl--

Column 9, line 39 – Replace "83 uL" with --83 μL--

Column 10, line 5 – Replace "100 uL" with --100 μL--

Column 10, line 6 – Replace "diisopropyl" with --di-isopropyl--

Column 10, line 6 – Replace "83 uL" with --83 μL--

UNITED STATES PATENT AND TRADEMARK OFFICE
CERTIFICATE OF CORRECTION

PATENT NO.       : 7,776,999 B2
APPLICATION NO.  : 11/787078
DATED            : August 17, 2010
INVENTOR(S)      : M. Uljana Mayer-Cumblidge et al.

It is certified that error appears in the above-identified patent and that said Letters Patent is hereby corrected as shown below:

<u>Title Page,</u>
Item [54], Title, the word "A" (as inserted by the Certificate of Correction issued May 29, 2012) should be deleted and title is reinstated to read -- CYANINE-BASED PROBE\TAG-PEPTIDE PAIR FOR FLUORESCENCE PROTEIN IMAGING AND FLUORESCENCE PROTEIN IMAGING METHODS --.

Signed and Sealed this
Nineteenth Day of June, 2012

David J. Kappos
*Director of the United States Patent and Trademark Office*

SEQUENCE LISTING

<160> NUMBER OF SEQ ID NOS: 4

<210> SEQ ID NO 1
<211> LENGTH: 5
<212> TYPE: PRT
<213> ORGANISM: Artificial
<220> FEATURE:
<223> OTHER INFORMATION: Synthetic

<400> SEQUENCE: 1

Lys Ala Glu Ala Ala
1               5

<210> SEQ ID NO 2
<211> LENGTH: 9
<212> TYPE: PRT
<213> ORGANISM: Artificial
<220> FEATURE:
<223> OTHER INFORMATION: Synthetic

<400> SEQUENCE: 2

Cys Cys Lys Ala Glu Ala Ala Cys Cys
1               5

<210> SEQ ID NO 3
<211> LENGTH: 6
<212> TYPE: PRT
<213> ORGANISM: Artificial
<220> FEATURE:
<223> OTHER INFORMATION: synthetic

<400> SEQUENCE: 3

Cys Cys Pro Gly Cys Cys
1               5

<210> SEQ ID NO 4
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (3)..(7)
<223> OTHER INFORMATION: Xaa can be any naturally occurring amino acid

<400> SEQUENCE: 4

Cys Cys Xaa Xaa Xaa Xaa Xaa Cys Cys
1               5